(12) United States Patent
Klare et al.

(10) Patent No.: US 6,818,725 B2
(45) Date of Patent: Nov. 16, 2004

(54) DENTAL MATERIALS BASED ON SUBSTITUTED IMINOOXADIAZINE DIONE DERIVATIVES

(75) Inventors: Martin Klare, Dortmund (DE); Andreas Radl, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 10/364,142

(22) Filed: Feb. 10, 2003

(65) Prior Publication Data

US 2003/0166741 A1 Sep. 4, 2003

(30) Foreign Application Priority Data

Feb. 27, 2002 (DE) .......................... 102 08 396

(51) Int. Cl.⁷ ............................................. C08G 18/79
(52) U.S. Cl. ..................... 528/73; 525/131; 523/109; 522/167
(58) Field of Search .......................... 525/131; 528/73; 523/109; 522/167

(56) References Cited

U.S. PATENT DOCUMENTS

| 3,860,556 A | | 1/1975 | Taylor | |
| 5,591,786 A | * | 1/1997 | Oxman et al. | 523/109 |
| 5,717,091 A | * | 2/1998 | Richter et al. | 544/67 |
| 5,914,383 A | * | 6/1999 | Richter et al. | |
| 6,191,181 B1 | * | 2/2001 | Weikard et al. | 522/174 |
| 2003/0187091 A1 | * | 10/2003 | Moszner et al. | 523/116 |

FOREIGN PATENT DOCUMENTS

| DE | 38 04 154 A1 | 8/1988 |
| DE | 195 05 351 A1 | 8/1996 |
| DE | 196 11 849 A1 | 10/1997 |
| DE | 197 34 048 A1 | 2/1999 |
| DE | 198 58 817 A1 | 6/2000 |
| DE | 198 58 818 A1 | 6/2000 |
| EP | 0 761 670 A2 | 3/1997 |
| EP | 1 002 818 A1 | 5/2000 |
| EP | 1 222 910 A2 | 7/2002 |

OTHER PUBLICATIONS

Richter et al., "Isocyanate und Isomerie," *Farbe & Lack*, 106:60–72 (2000).

Falbe, eds. *Römpp Chemie Lexikon*, Stuttgart, Germany:Georg Thieme Verlag, vol. 2, pp. 824–825 and vol. 3, pp. 2060–2061 (1990).

* cited by examiner

*Primary Examiner*—Rachel Gorr
(74) *Attorney, Agent, or Firm*—Nixon Peabody LLP

(57) ABSTRACT

The invention relates to dental materials which contain an iminooxadiazine dione derivative with at least two free isocyanate groups and a hydroxyl compound with at least two OH groups.

12 Claims, 1 Drawing Sheet

DENTAL MATERIALS BASED ON SUBSTITUTED IMINOOXADIAZINE DIONE DERIVATIVES

The present invention relates to dental materials which contain substituted iminooxadiazine dione derivatives.

Varnishes and dyes based on isocyanates have been long known. These cure by polyaddition of a diol, such as 1,4-butylene glycol, to a diisocyanate, such as hexamethylene diisocyanate, accompanied by development of polyurethanes. The use of isocyanates in dental materials is likewise known. Here the isocyanates are often combined with (meth)acrylates, so that a two-phase curing of the material by diisocyanate polyaddition and radical polymerization is possible. In this way the dental material can be initially pre-cured by polyurethane formation after introduction into the patient's mouth and modeled in the initially cured state and any resulting excess can be easily removed before it is then finally cured by radical polymerization.

It has been shown however that technically significant diisocyanates, such as e.g. hexamethylene diisocyanate (HDI), isophorone diisocyanate (IPDI) and bis-(4-isocyanatocyclohexyl)-methane ($H_{12}$MDI), both in monomeric and in oligomeric form, i.e. for example in the form of trimers, are often sensitive to temperature and moisture. In addition, the oligomeric forms mostly have high viscosities which make their further processing difficult. Dental materials often contain for example a greater or lesser filler proportion, which has to be homogeneously worked into the material in order to achieve the most uniform properties possible. The incorporation of the filler is made difficult by viscous monomers. In addition, the filler content is limited in the case of high viscosity so that an adaptation of the properties of the material to the desired application purpose is possible only to a limited extent.

The object of the invention is to make dental materials available which are insensitive to moisture and whose filler content can accordingly be matched exactly to the requirements.

This object is achieved by dental materials which contain at least one iminooxadiazine dione derivative and at least one hydroxyl compound with at least two OH groups. By iminooxadiazine dione derivatives are meant derivatives of 6-imino-1,3,5-oxadiazine-2,4-dione, which have at least 2, preferably at least 3 free isocyanate groups.

Dental materials are preferred which contain at least one iminooxadiazine dione derivative with the formula

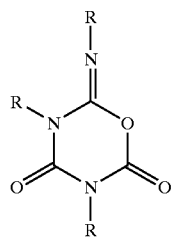

in which R is a $C_1$ to $C_{16}$ alkyl, $C_1$ to $C_{16}$ cycloalkyl and/or $C_1$ to $C_{16}$ alkylcycloalkyl radical which has 1 to 4, preferably 1 to 2, most preferably 1 isocyanate group.

The preferred iminooxadiazine dione derivatives are asymmetric trimers of diisocyanates which form when three diisocyanate monomers each combine via an isocyanate group and the second isocyanate group is retained. The substituted 6-imino-1,3,5-oxadiazine-2,4-diones used according to the invention are therefore also called diisocyanate trimers in the following, for the sake of simplicity.

By alkylcycloalkyl radicals are meant groups which contain both alkyl and cycloalkyl radicals. Alkyl, cycloalkyl and alkylcyclalkyl radicals with 4 to 14 and in particular 6 to 13 carbon atoms are preferred. Quite particularly preferred iminooxadiazine dione derivatives are the asymmetric trimers of hexamethylene diisocyanate. By diisocyanate trimers according to the invention are preferably meant compounds which are formed by three identical monomers.

Further iminooxadiazine dione derivatives preferred according to the invention and their preparation are described in DE 196 11 849 A2, DE 197 34 048 A2 and by Richter and Mertes, Farbe & Lack 106 (9/2000) pages 60 ff.

The iminooxadiazine dione derivatives used according to the invention can be cured like the monomeric compounds by isocyanate polyaddition and show an isocyanate reactivity comparable with the symmetric diisocyanate trimers. By the symmetric trimers are meant the corresponding isocyanuric acid derivatives which have a symmetric arrangement of ring atoms and substituents.

The iminooxadiazine dione derivatives and in particular the asymmetric diisocyanate trimers are characterized compared with the symmetric trimers by a clearly increased moisture—and temperature—stability and a lower viscosity. For example, the viscosity of the asymmetric trimer of hexamethylene diisocyanate (R=—$(CH_2)_6$—NCO) is lower by a factor of two than the viscosity of the corresponding symmetric trimer. The lower viscosity facilitates the incorporation of filler into the material and simultaneously allows the use of higher filler amounts.

The iminooxadiazine dione derivatives preferred according to the invention have a viscosity of <2000 mPas, preferably of <1500 mPas and particularly preferably roughly 1000±200 mPas. Unless stated otherwise, the viscosity is measured according to DIN EN 3219/A3.

The dental materials according to the invention preferably contain at least 5 to 50 wt.-%, particularly preferably 7 to 40 wt.-% and quite particularly preferably 9 to 30 wt.-% of the asymmetric trimer, relative to the total mass of the material.

The dental materials according to the invention contain, as further component, at least one hydroxyl compound which, together with the iminooxadiazine dione derivative, forms a polyurethane by diisocyanate polyaddition.

Polyols in particular are suitable as hydroxyl compounds. By polyols are meant compounds with 3 and more hydroxyl groups, the term hydroxyl group referring to alcoholic OH groups. Monomeric or polymeric aliphatic, alicyclic or aromatic compounds with 3 to 6 OH groups are particularly preferred.

Among the hydroxyl compounds with three OH groups, trimethylolethane, trimethylolpropane, trimethylolbutane, glycerol and the low-molecular adducts of ethylene and/or propylene oxide to the named compounds are to be emphasized as particularly suitable.

Preferred hydroxyl compounds with four OH groups are pentaerythritol and di-trimethylolpropane.

A preferred hydroxyl compound with six OH groups is di-pentaerythritol.

Furthermore aliphatic and/or cycloaliphatic diols can also be used, e.g. ethylene glycol, di- and triethylene glycol, 1,2- and 1,3-propanediol, di- and tripropylene glycol, 1,2 and 1,3 or 1,4 butanediol, 1,6 hexanediol, 2-methylpentanediol, neopentyl glycol, cyclohexanediol and dimethylolcyclohexane.

Preferred polymeric polyols are polyester polyols, polyether polyols and polyalcohols which contain both ester and ether groups, hydroxyl compounds being particularly preferred which have an equivalent weight of 50 to 1000, particularly preferably 70 to 400 per hydroxyl group.

Among the polymer polyols, compounds are furthermore preferred which have a branched structure.

Particularly suitable for the preparation of the dental materials according to the invention are hydroxyl compounds which, in addition to the hydroxyl groups, contain radically polymerizable groups and thus facilitate a cross-linking of the polyurethane chains formed by the diisocyanate polyaddition by radical polymerization. Vinyl, methacryl and/or acryl groups in particular can be considered as polymerizable groups.

The preferred hydroxyl compounds with radically polymerizable groups include the hydroxyethyl (meth)acrylates, such as e.g. 2-hydroxyethyl acrylate, 2-hydroxyethyl methacrylate, 2-hydroxypropyl methacrylate, 4-hydroxybutyl acrylate and 4-hydroxybutyl methacrylate.

A mixture of the abovementioned hydroxyl compounds can also be advantageously used as hydroxyl component, preferably a mixture of monomeric and polymeric hydroxyl compounds. A preferred mixture contains 28 to 38 wt.-%, preferably 30 to 36 wt.-% monomeric hydroxyl compound, in particular trimethylolpropane, and 62 to 72 wt.-%, preferably 64 to 70 wt.-% polymeric hydroxyl compound, in particular polyesters containing hydroxyl groups and/or polyalcohol containing ester and ether groups, the polymer components having a branched structure according to a further preferred version.

The hydroxyl compound content of the dental materials is based primarily on the amount of iminooxadiazine dione derivative. A content of 4 to 40 wt.-%, preferably 5 to 20 wt.-% and in particular 6 to 12 wt.-%, is preferred relative to the total mass of the material.

Dental materials which, along with the iminooxadiazine dione derivative, contain radically polymerizable hydroxyl compounds, can be cured in two stages. The active ingredients are preferably pre-cured in a first stage by the diisocyanate polyaddition. In the pre-cured state the materials are already relatively solid and dimensionally stable, but can still be modeled and excess material can be easily removed. The final curing takes place by radical polymerization.

Along with iminooxadiazine dione derivative and hydroxyl compound the dental materials according to the invention preferably additionally contain one or more radically polymerizable monomers. These can optionally be copolymerized with the hydroxyl compounds containing radically polymerizable groups. Materials which contain both radically polymerizable monomer and hydroxyl compounds with radically polymerizable groups are particularly suitable according to the invention.

Suitable in particular as radically polymerizable monomers are mono- and polyfunctional (meth)acrylates, i.e. compounds with one or more (meth)acrylate groups. The compounds named below are particularly preferred: 2,2-bis-[4-(2'-hydroxy-3'-methacryloxy-propoxy)phenylene] propane (bis-GMA), ethoxylated bisphenol-A-dimethacrylate, urethane dimethacrylates, mono-, di-, tri- and tetraethylene glycol dimethacrylates, neopentyl glycol dimethacrylates, 1,3-butanediol dimethacrylate, 1,6-hexanediol dimethacrylate, 2,2-bis[4-(2-hydroxy-3-acryloyloxypropane)phenyl]-propane or 2,2-bis[4-(acryloyloxy-ethoxy)phenyl]propane. Along with the aforementioned dimethacrylates the corresponding diacrylates are also preferred. Of the above monomers, those with two or more (meth)acrylate groups are particularly preferred, likewise monomer mixtures which contain at least one monomer with two or more (meth)acrylate groups as cross-linkers.

The dental materials according to the invention also preferably contain one or more fillers. There can be used as fillers practically all known and proven fillers used hitherto in dental materials, the size of the filler particles preferably being below 200 $\mu$m, preferably in the range from 10 nm to 200 $\mu$m, and the filler should be silanized before incorporation into the dental materials, preferably with $\gamma$-methacryloxypropyl-trimethoxy silane.

The preferred fillers include in particular inorganic glass, glass ceramic and ceramic powders with an average particle size of 0.01 to 10 $\mu$m, preferably 0.1 to 5 $\mu$m, such as e.g. fine-particled boronsilicate glasses, Yb, Zr and La glasses, alkali and alkaline-earth silicates, as well as X-ray opaque fillers, such as e.g. ytterbium trifluoride and bismuth carbonate, pyrogenic silicic acid and precipitated silicic acid, filled and unfilled organic fillers based on ground poly(meth)acrylates, polycarbonates or polyepoxides as well as mixtures of the named materials. Fillers based on cured organic materials are also called isofillers. The particle size of isofillers is preferably in the range from >10 $\mu$m to 200 $\mu$m, in particular >10 $\mu$m to 50 $\mu$m. A further group of preferred fillers is zeolites, zeolites of type A being particularly preferred.

The dental materials according to the invention preferably also contain a catalyst for the urethane reaction and/or an initiator for the radical polymerization.

Different organotin compounds can be used as catalysts for the urethane reaction. Preferred catalysts are dibutyltin oxide, dioctyltin oxide, dibutyltin glycolate, diacetate, dilaurate, maleate, dilauryltin diacetate, dibutyltin maleate ester, di-n-octyltin maleate ester, dibutyltin alkyl mercaptide, dibutyltin mercapto ester, tributyltin laurate and di-n-octyltin carboxylates.

Dibenzoyl peroxide (DBPO), di-p-chlorobenzoyl peroxide, tert.-butylperoxy benzoate and cumene hydroperoxide are particularly suitable as initiators for the radical polymerization. Initiators for the photopolymerization, such as camphorquinone, are likewise preferred. Further suitable photoinitiators are described in U.S. Pat. No. 4,746,686. Preferred initiators are dibenzoyl peroxide and camphorquinone.

The initiators, such as for example the named peroxides, are preferably used in combination with polymerization accelerators. Preferred accelerators are tertiary amines, such as triethanolamine, N,N,3,5-tetramethylaniline, dimethylamino-benzoic acid ester, dimethyl-p-toluidine or dihydroxyethyl-p-toluidine.

If the peroxides are used alone, then heat-curing materials are obtained. Materials which are cold-curing or self-curing materials are obtained by combining the peroxides with accelerators. Through the combination of photoinitators with initiators for the hot or cold curing, dual-curable materials become accessible.

Along with the named components the dental materials according to the invention can contain stabilizers and additives, such as e.g. agents for the adjustment of the viscosity, pigments, plasticizers and antimicrobial additives.

Benzoquinone, hydroquinone, hydroquinone monomethyl ether, 2,6-di-tert.-butyl-p-cresol (butylated hydroxy toluene, BHT), phenol and phenolic compounds as well as chloranil are preferred as stabilizers. The stabilizers are intended to prevent a premature polymerization of the material. A preferred stabilizer is 2,6-di-tert.-butyl-p-cresol.

The dental materials according to the invention are preferably prepared in the form of two components, a first and a second component. In this way reactive constituents of the material, such as e.g. iminooxadiazine dione derivative and hydroxyl compound or initiator and accelerator, can be distributed among different components. The first component preferably contains the hydroxyl compound and the second component the iminooxadiazine dione derivative so that, by mixing the components, the diisocyanate polyaddition can be triggered. When using initiator/accelerator systems the radical polymerization can also be started by mixing the components.

Along with the hydroxyl compound, the first component (base paste) preferably also contains, if present, radically polymerizable monomer, filler, catalyst, stabilizer and additive.

According to a particularly preferred version of the invention the first component contains the following constituents:
3 to 85 wt.-%, preferably 31 to 79 wt.-% and particularly preferably 46 to 72 wt.-% hydroxyl compound,
15–50 wt.-%, preferably 20 to 40 wt.-%, particularly preferably 25 to 35 wt.-% radically polymerizable monomer,
0–75 wt.-%, preferably 0.2 to 4 wt.-%, particularly preferably 0.5 to 2 wt.-% filler,
0–10 wt.-%, preferably 0.2 to 4 wt.-%, particularly preferably 0.5 to 2 wt.-% catalyst for the diisocyanate polyaddition,
0–10 wt.-%, preferably 1.5 to 6 wt.-%, particularly preferably 2 to 5 wt.-% accelerator for the radical polymerization,
0–10 wt.-%, preferably 0 to 3 wt.-%, particularly preferably 0.01 to 0.15 wt.-% stabilizer and
0 to 15 wt.-%, preferably 0 to 12 wt.-%, particularly preferably 0.01 to 10 wt.-% additive,
each relative to the total mass of the first component.

Along with the iminooxadiazine dione derivative the second component (catalyst paste) also preferably contains, if present, filler, stabilizer, initiator and additives.

According to a particularly preferred version of the invention the second component contains the following constituents:
15–100 wt.-%, preferably 20 to 100 wt.-%, particularly preferably 25 to 100 wt.-% and quite particularly preferably 35 to 98 wt.-% iminooxadiazine dione derivative,
0 to 95 wt.-%, preferably 0 to 75 wt.-% and particularly preferably 5 to 50 wt.-% filler, zeolite and highly-dispersed silicic acid being preferably used as filler in the amounts defined below:
0–75 wt.-%, preferably 0 to 60 wt.-%, particularly preferably 0 to 25 wt.-% highly-dispersed silicic acid,
0–75 wt.-%, preferably 5 to 50 wt.-%, particularly preferably 10 to 25 wt.-% zeolite,
0–5 wt.-%, preferably 0 to 4.5 wt.-%, particularly preferably 2 to 4.5 wt.-% initiator for the radical polymerization, and
0–5 wt.-%, preferably 0.005 to 2 wt.-%, particularly preferably 0.01 to 0.5 wt.-% stabilizer,
each relative to the total mass of the second component.

Pyrogenic silicic acid is particularly suitable as highly-dispersed silicic acid.

During the preparation of the iminooxadiazine dione derivatives, usually symmetric trimers and also higher oligomers form. As these likewise have reactive isocyanate groups and thus have to be incorporated into the polymer network during the diisocyanate polyaddition, they do not necessarily have to be separated from the iminooxadiazine dione derivative. By higher oligomers are meant compounds which are formed from four and more diisocyanate monomers. The total quantity of symmetric trimers and higher oligomers should however be as small as possible and amount to at most 70 wt.-%, preferably at most 50 wt.-%, particularly preferably at most 20 wt.-% and quite particularly preferably at most 5 wt.-%, each relative to the total mass of the second component. The level of symmetric trimers and higher oligomers in the total material can be determined via the mixing ratio of first and second component. Ideally, the materials contain no symmetric trimers or higher oligomers.

The dental materials according to the invention are preferably suitable for the preparation of crowns, bridges and cements, in particular for provisional crowns and bridges.

Two-component compositions for dental materials are preferably prepared as paste/paste systems, i.e. the viscosity of the monomer or monomers, filler proportion and additive content are measured such that the respective component has a paste-like consistency.

The composition of the individual components is preferably measured such that this can be used in a mixture ratio of 10:1 to 1:1, preferably 4:1 to 2:1 and in particular 4:1 (relative to the volume). A greater amount of component 1 (base paste) is preferably mixed with a smaller amount of component 2 (catalyst paste).

The stated mixture ratio ensures that the materials according to the invention can be incorporated without any problems into mixing apparatus customary in the trade. These are automatic mixing apparatuses which normally include a static mixer and double cartridges. The components of the dental material are stored in separate chambers of the automix cartridges. If necessary, the pastes are pressed out of the separate chambers through a static mixer. The static mixer normally consists of a mixing chamber and a static mixing screw which causes the individual paste strands from the paste chambers to be combined, separated, reunited and thus thoroughly mixed. The pastes are extruded in a preset mixing ratio which is determined by the volume ratio of the mixing chambers.

Mixing ratio and composition of the components are preferably matched so that asymmetric trimer content of the total composition is in the above stated ranges, i.e. at least 5 wt.-%, preferably 5 to 50 wt.-%, particularly preferably 7 to 40 wt.-% and quite particularly preferably 9 to 30 wt.-%.

The invention is explained in more detail in the following with reference to embodiments.

EXAMPLES

Example 1

Comparison of the Sensitivity to Moisture of Symmetric and Asymmetric Diisocyanate Trimers The asymmetric hexamethylene diisocyanate (HDI) trimer 3,5-bis(6-isocyanato-hexyl)-6-[(6-isocyanatohexyl)imino]-1,3,5-oxadiazine-2,4-dione (Desmodur® VP LS2294, Bayer AG) and the symmetric isocyanurate trimer of HDI (Desmodur® N 3300, Bayer AG) were stored separately each in 10-ml containers at 37° C. in a steam-saturated atmosphere and the thickness of the film forming through reaction of the isocyanate derivatives with water was measured over a period of one week.

Figure 1:
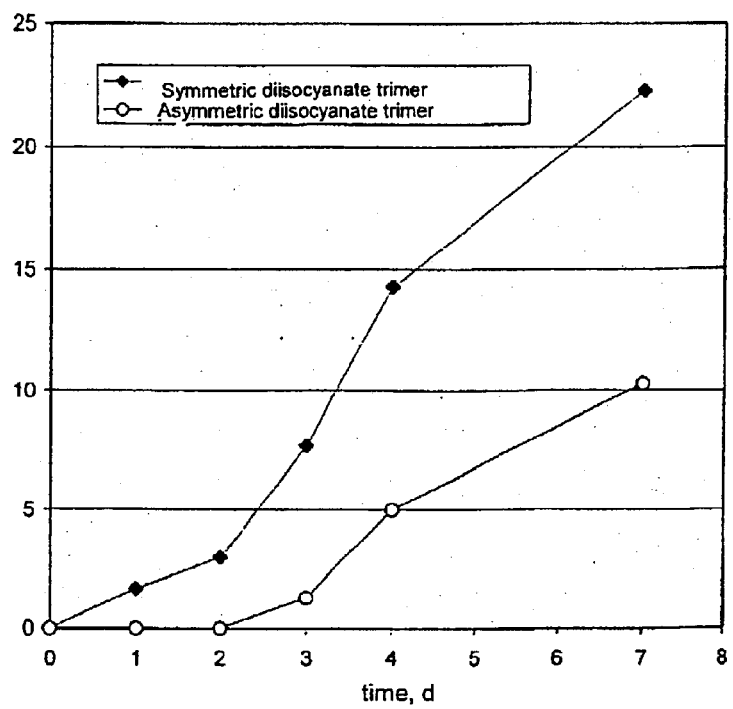
FIG. 1 is a graphic representation of film layer thickness in relation to time.

In FIG. 1 the layer thickness in relation to time is graphically represented. It is to be recognized that the layer thickness of the asymmetric diisocyanate trimer (Desmodur® VP LS2294) increases much more slowly than the layer thickness of the symmetric trimer (Desmodur® N 3300). In the case of the asymmetric diisocyanate trimer, skin formation is first perceptible only after 3 days under the chosen conditions, and after one week is less than half of the symmetric variants.

Example 2
Self-curing Material for the Preparation of Crowns and Bridges

A two-component material with the following composition was prepared:

| Constituent | Proportion |
|---|---|
| Base paste: | |
| Monomer mixture[1] | 27.50 wt.-% |
| Hydroxyl component[2] | 9.60 wt.-% |
| Filler | |
| Barium glass, silanised[3] | 30.30 wt.-% |
| Isofiller[4] | 16.00 wt.-% |
| Pyrogenic silicic acid[5] | 1.90 wt.-% |
| Catalyst (di-n-octyltin carboxylate) | 0.75 wt.-% |
| Stabilizer (BHT) | 0.05 wt.-% |
| Polymerization accelerator (dihydroxyethyl-p-toluidine) | 4.40 wt.-% |
| Zeolite paste[6] | 9.50 wt.-% |
| Catalyst paste: | |
| Asymmetric trimer*) | 95.90 wt.-% |
| Dibenzoyl peroxide | 4.00 wt.-% |
| Stabilizer (BHT) | 0.10 wt.-% |

[1]10 wt.-% bis-GMA, 65.5 wt.-% urethane dimethacrylate, 24.5 wt.-% triethylene glycol dimethacrylate, relative to the mass of the monomeric component
[2]Polyalcohol mixture with 32.8 trimethylolpropane, 60.5 wt.-% branched polyalcohol with ester and ether groups (hydroxyl content according to DIN 53402 7.1 ± 0.5; Desmophen 1145, Bayer AG) and 6.7 wt.-% branched polyester containing hydroxyl groups (hydroxyl content according to DIN 53402 8.6 ± 0.3; Desmophen 800, Bayer AG), relative to the mass of the hydroxyl component
[3]Particle size 5.5 μm ± 2 μm
[4]Fine-particled polymerisate based on 70 wt.-% pyrogenic silicic acid (BET surface 50 m²/g, average particle size 40 nm), 23 wt.-% 7,7(9),9-trimethyl-4,13-dioxo-3,14-dioxa-5,12-diazohexadecane-1,16-diyl-dimethacrylate, 6.4 wt.-% 1,10-decanediol dimethacrylate and 0.6 wt.-% dibenzoyl peroxide, relative to the mass of the isofiller
[5]BET surface 140 m²/g, primary particle size 10–30 nm, particle size of the agglomerates 10–100 μm, modified with —OSi(CH₃)₃ (HDK 2000)
[6]Mixture of 50 wt.-% sodium aluminosilicate, 14 wt.-% pyrogenic silicic acid, 3.6 wt.-% bis-GMA, 23.4 wt.-% urethane dimethacrylate and 9 wt.-% triethylene glycol dimethacrylate, relative to the mass of the zeolite paste
*) 3,5-bis(6-isocyanato-hexyl)-6-[(6-isocyanato-hexyl)imino]-1,3,5-oxadiazine-2,4-dione (Desmodur® VP LS 2294)

Base paste and catalyst paste were mixed together in a ratio of 4:1. Both the diisocyanate polyaddition and the radical polymerization are triggered by the mixing of the components, i.e. the material involved which is completely self-curing.

After curing, the material has an E-modulus of 1856 MPa and a bending strength of 66 MPa. Both values are within the ranges customary for commercial provisional dental materials (1600 to 3200 MPa for the E-modulus and 60 to 85 MPa for the bending strength). Unless stated otherwise E-modulus and bending strength were determined in this and all other examples according to EN ISO 4049.

Example 3
Self- and Light-curing Material for the Preparation of Crowns and Bridges A two-component material with the following composition was prepared. Unless stated otherwise the same materials were used as in Example 2.

| Constituent | Proportion |
|---|---|
| Base paste: | |
| Monomer mixture[1] | 29.60 wt.-% |
| Filler | |
| Barium glass, silanized | 32.50 wt.-% |
| Isofiller | 15.95 wt.- |
| Pyrogenic silicic acid | 1.90 wt.-% |
| Hydroxyl component | 9.65 wt.-% |
| Zeolite paste | 9.50 wt.-% |
| Tin catalyst | 0.75 wt.-% |
| Pigments (TiO₂) | 0.10 wt.-% |
| Additives[2] | 0.05 wt.-% |
| Catalyst paste: | |
| Asymmetric trimer*) | 100 wt.-% |

[1]Mixture from Example 2 + BHT, camphorquinone, ethyl-p-dimethylaminobenzoate
[2]Plasticizer (dibutyl phthalate), antimicrobial additives (triclosan, chlorohexidine), antifoaming agents (methylpolysiloxanes)
*) 3,5-bis (6-isocyanato-hexyl)-6-[(6-isocyanato-hexyl)imino]-1,3,5-oxadiazine-2,4-dione (Desmodur® VP LS 2294)

Base paste and catalyst paste were mixed together in a ratio of 4:1. The diisocyanate polyaddition is triggered by the mixing of the components, the radical polymerization is initiated by light.

After complete curing, the material had an E-modulus of 4034 MPa and a bending strength of 111 MPa. Both values clearly exceed the values customary in commercial provisional dental materials.

Example 4
Influence of Different Sn Organyls on the Diisocyanate Polyaddition In order to determine the influence of the catalyst on the speed of the diisocyanate polyaddition, dental materials based on the asymmetric diisocyanate trimer of HDI (Desmodur® VP LS2294, Bayer AG) were prepared. As base paste the composition described in Example 3 was used, the catalysts stated below being used for the preparation of the paste, the pure diisocyanate trimers serving in each case as catalyst paste. Base paste and catalyst paste were mixed together in the ratio 4:1.

Catalysts used for the preparation of the base paste:

| Name | Catalyst |
|---|---|
| Cat. 1 | Dibutyltin mercaptide |
| Cat. 2 | Dibutyltin dilaurate |
| Cat. 3 | Di-n-butyltin dilaurate |
| Cat. 4 | Di-n-octyltin dilaurate |
| Cat. 5 | Di-n-octyltin maleate ester |
| Cat. 6 | Di-n-octyltin carboxylate |

Figure 2:
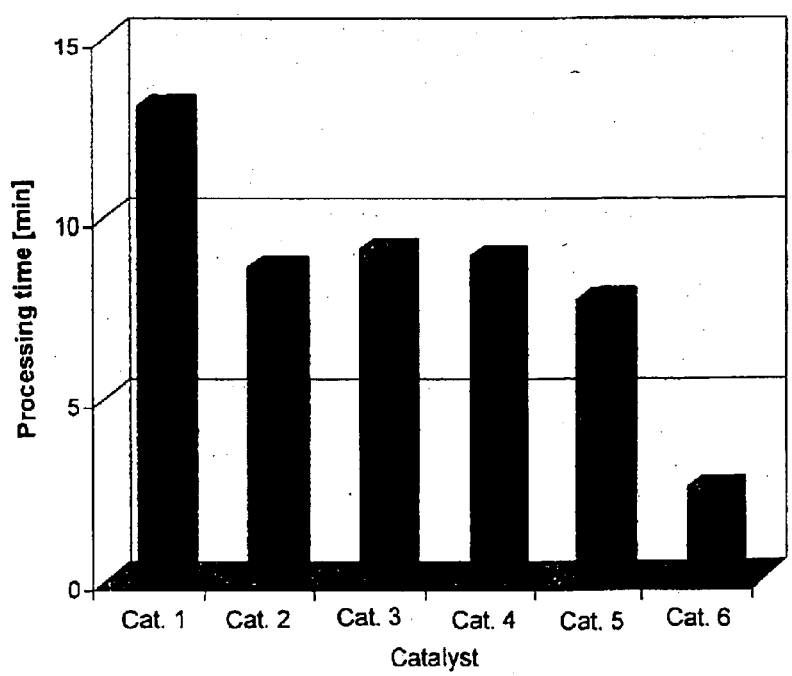
FIG. 2 is a graphic representation of processing time in relation to type of catalyst.

The quantity of catalyst used for the preparation of the materials was the same in all cases. For each material, the processing time available was measured by means of a rheometer using the tangent method (viscosity according to DIN 53019/1). The results achieved are represented in FIG. 2.

The results found show that the processing time strongly depends on the type of catalyst. Through the selection of the catalyst the processing time of the dental materials can thus be adapted to the respective results.

Example 5
Self- and Light-curing Material for the Preparation of Provisional Crowns and Bridges A two-component material with the following composition was prepared. Unless stated otherwise the same materials were used as in Example 2.

| Constituent | Proportion |
|---|---|
| Base paste: | |
| Monomer mixture (as Example 3) | 29.60 wt.-% |
| Filler | |
| Barium glass, silanized | 32.50 wt.-% |
| Isofiller | 15.95 wt.-% |
| Pyrogenic silicic acid (HDK 2000) | 1.90 wt.-% |
| Zeolite paste | 9.50 wt.-% |
| Hydroxyl compound | 9.65 wt.-% |
| Tin catalyst | 0.75 wt.-% |
| Pigments | 0.10 wt.-% |
| Additives | 0.05 wt.-% |
| Catalyst paste: | |
| Asymmetric trimer*) | 50.0 wt.-% |
| Zeolite paste | 50.0 wt.-% |

*) 3,5-bis(6-isocyanato-hexyl)-6-[(6-isocyanato-hexyl)imino]-1,3,5-oxadiazine-2,4-dione (Desmodur ® VP LS 2294)

Base paste and catalyst paste were mixed together in the ratio of 1:1. The diisocyanate polyaddition is triggered by the mixing of the components, the radical polymerization is initiated by light.

After complete curing the material had an E-modulus of 4691 MPa and a bending strength of 79 MPa. Both values clearly exceed the values customary in commercial provisional dental materials.

Example 6
Self- and Light-curing Material for the Preparation of Provisional Crowns and Bridges A two-component material with the following composition was prepared. Unless stated otherwise the same materials were used as in Example 2.

| Constituent | Proportion |
|---|---|
| Base paste: | |
| Monomer mixture (as Example 3) | 29.60 wt.-% |
| Filler | |
| Barium glass, silanized | 32.50 wt.-% |
| Isofiller | 15.95 wt.-% |
| Pyrogenic silicic acid (HDK 2000) | 1.90 wt.-% |
| Zeolite paste | 9.50 wt.-% |
| Hydroxyl compound | 9.65 wt.-% |
| Tin catalyst | 0.75 wt.-% |
| Pigments | 0.10 wt.-% |
| Additives | 0.05 wt.-% |
| Catalyst paste: | |
| Asymmetric trimer*) | 66.0 wt.-% |
| Zeolite paste | 34.0 wt.-% |

*) 3,5-bis(6-isocyanato-hexyl)-6-[(6-isocyanato-hexyl)imino]-1,3,5-oxadiazine-2,4-dione (Desmodur ® VP LS 2294)

Base paste and catalyst paste were mixed together in the ratio of 2:1. The diisocyanate polyaddition is triggered by the mixing of the components, the radical polymerization is initiated by light.

After complete curing the material had an E-modulus of 3973 MPa and a bending strength of 63 MPa. The E-modulus clearly exceeds the values customary in commercial provisional dental materials, the bending strength lies in the customary range.

Example 7
Self-curing Dental Cement

A two-component material with the following composition was prepared. Unless stated otherwise the same materials were used as in Example 2.

| Constituent | Proportion |
|---|---|
| Base paste: | |
| Monomer mixture (mixture from Example 2 + BHT) | 37.20 wt.-% |
| Filler | |
| Barium glass, silanized | 24.40 wt.-% |
| Pyrogenic silicic acid, silanized | 8.60 wt.-% |
| Ytterbium trifluoride (X-ray opaque filler) | 9.10 wt.-% |
| Zeolite paste | 8.50 wt.-% |
| Hydroxyl compound | 8.55 wt.-% |
| Polymerization accelerator (dihydroxyethyl-p-toluidine) | 2.95 wt.-% |
| Tin catalyst | 0.65 wt.-% |
| Additives | 0.05 wt.-% |
| Catalyst paste: | |
| Asymmetric trimer*) | 48.9 wt.-% |
| Zeolite paste | 50.0 wt.-% |
| Dibenzoyl peroxide | 1.0 wt.-% |
| Stabilizer (BHT) | 0.1 wt.-% |

*) 3,5-bis(6-isocyanato-hexyl)-6-[(6-isocyanato-hexyl)imino]-1,3,5-oxadiazine-2,4-dione (Desmodur ® VP LS 2294)

Base paste and catalyst paste were mixed together in the ratio of 1:1. Both the diisocyanate polyaddition and the radical polymerization are triggered by the mixing of the components, i.e. the material involved is completely self-curing.

After complete curing the material had a compressive strength of 120 MPa. This value clearly exceeds the values (60 to 85 MPa) customary in commercial provisional dental materials. Unless stated otherwise the compressive strength in these and in all other examples was determined according to EN 29917 with a Zwick universal testing machine.

Example 8
Self- and Light-curing Dental Cement

A two-component material with the following composition was prepared. Unless otherwise stated the same materials were used as in Example 2.

| Constituent | Proportion |
|---|---|
| Base paste: | |
| Monomer mixture | 40.85 wt.-% |
| Filler | |
| Barium glass filler, silanized | 22.20 wt.-% |
| Pyrogenic silicic acid, silanized | 9.80 wt.-% |

-continued

| Constituent | Proportion |
|---|---|
| Ytterbium trifluoride | 9.10 wt.-% |
| Zeolite paste | 8.90 wt.-% |
| Hydroxyl compound | 8.50 wt.-% |
| Tin catalyst | 0.65 wt.-% |
| Catalyst paste: | |
| Asymmetric trimer*) | 50.0 wt.-% |
| Zeolite paste | 50.0 wt.-% |

*) 3,5-bis(6-isocyanato-hexyl)-6-[(6-isocyanato-hexyl)imino]-1,3,5-oxadiazine-2,4-dione (Desmodur ® VP LS 2294)

Base paste and catalyst paste were mixed together in the ratio of 1:1. The diisocyanate polyaddition is triggered by the mixing of the components, the radical polymerization is initiated by light.

After complete curing the material had a compressive strength of 89 MPa. This value exceeds the values customary in commercial provisional dental materials.

What is claimed is:

1. Dental material containing an iminooxadiazine dione derivative with at least two free isocyanate groups, at least one hydroxyl compound with at least two OH groups, and one or more radically polymerizable monomers.

2. Dental material according to claim 1, wherein said iminooxadiazine dione derivative has the formula

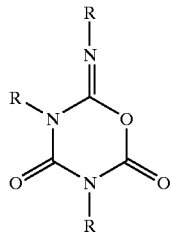

in which R is a $C_1$ to $C_{12}$ alkyl radical which contains at least one isocyanate group.

3. Dental material according to claim 1, wherein said iminooxadiazine dione derivative is present in an amount from 5 to 50 wt.-%.

4. Dental material according to claim 1, wherein said hydroxyl compound is a monomeric or polymeric aliphatic, alicyclic or aromatic compound with 2 to 6 OH groups.

5. Dental material according to claim 4, wherein said hydroxyl compound additionally contains radically polymerizable groups.

6. Dental material according to claim 5, wherein said hydroxyl compound contains at least one vinyl, methacryl and/or acryl group.

7. Dental material containing an iminooxadiazine dione derivative of the formula

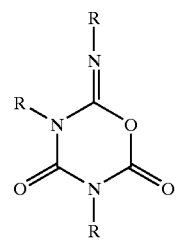

in which R is a $C_1$ to $C_{12}$ alkyl radical which contains at least one isocyanate group, at least one monomeric or polymeric aliphatic, alicyclic or aromatic compound with 2 to 6 OH groups, and one or more fillers, wherein the iminooxadiazine dione derivative is present in an amount of from 5 to 50 wt.-%.

8. Dental material according to claim 1, further comprising at least one of a urethane reaction catalyst and a radical polymerization initiator.

9. Dental material according to claim 1, further comprising a first and a second component, the first component containing said at least one hydroxyl compound and the second component containing said iminooxadiazine dione derivative.

10. Dental material according to claim 9, wherein said first component contains

| | |
|---|---|
| 3–85 wt.-% | hydroxyl compound, |
| 15–50 wt.-% | radically polymerizable monomer, |
| 0–75 wt.-% | filler, |
| 0–10 wt.-% | catalyst for the diisocyanate polyaddition, |
| 0–10 wt.-% | accelerator for the radical polymerization, |
| 0–10 wt.-% | stabilizer and |
| 0–15 wt.-% | additives | each relative to the total mass of the first component, and the second component contains

| | |
|---|---|
| 15–100 wt.-% | iminooxadiazine dione derivative, |
| 0–95 wt.-% | filler, |
| 0–5 wt.-% | initiator for the radical polymerization, and |
| 0–5 wt.-% | stabilizer | each relative to the total mass of the second component.

11. A method for the preparation of dental materials, comprising using an iminooxadiazine dione derivative with at least two free isocyanate groups, at least one hydroxyl compound with at least two OH groups, and one or more radically polymerizable monomers, for the preparation of dental materials.

12. The method according to claim 11, wherein said dental materials are one of crowns, bridges and cements.

* * * * *